(12) United States Patent
Lee et al.

(10) Patent No.: US 11,834,560 B2
(45) Date of Patent: Dec. 5, 2023

(54) WATER DEGRADABLE FILM CONTAINING HYALURONIC ACID OR SALT THEREOF AND POLYPHENOL COMPOUNDS

(71) Applicant: Korea Research Institute of Chemical Technology, Daejeon (KR)

(72) Inventors: Jae-Hyeok Lee, Daejeon (KR); Sun-Hyun Park, Daejeon (KR); Ki-Suk Kim, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 367 days.

(21) Appl. No.: 16/934,475

(22) Filed: Jul. 21, 2020

(65) Prior Publication Data

US 2021/0070951 A1    Mar. 11, 2021

(51) Int. Cl.
*C08J 5/18*      (2006.01)
*C08K 5/13*      (2006.01)
*C08L 5/08*      (2006.01)
*B82Y 30/00*     (2011.01)
*B82Y 40/00*     (2011.01)

(52) U.S. Cl.
CPC ..................... *C08J 5/18* (2013.01); *C08K 5/13* (2013.01); *C08L 5/08* (2013.01); *B82Y 30/00* (2013.01); *B82Y 40/00* (2013.01); *C08J 2305/08* (2013.01); *C08L 2201/06* (2013.01); *C08L 2203/16* (2013.01)

(58) Field of Classification Search
CPC ........ C08J 5/18; A61K 31/12; A61K 31/7024; A61K 31/353; A61P 9/00; C08L 5/08; C08K 5/13
See application file for complete search history.

(56) References Cited

U.S. PATENT DOCUMENTS

2009/0143331 A1   6/2009  Stroumpoulis et al. ........ 514/56
2011/0311592 A1  12/2011  Birbara .......................... 424/400

FOREIGN PATENT DOCUMENTS

| JP | 2014-214133 | | 11/2014 |
| JP | 2014214133 A | * | 11/2014 |
| JP | 2018-511377 | | 4/2018 |
| KR | 10-2009-0040979 | | 4/2009 |
| KR | 10-2011-0035136 | | 4/2011 |
| KR | 2015-16614 | | 1/2015 |
| KR | 10-2017-0128351 | | 11/2017 |
| KR | 10-2019-0103559 | | 9/2019 |
| KR | 20190103559 A | * | 9/2019 |
| WO | 2011/004962 | | 1/2011 |
| WO | 2012/054090 | | 4/2012 |

OTHER PUBLICATIONS

Barbarisi et al ("Novel nanohydrogel of hyaluronic acid loaded with quercetin alone and in combination with temozolomide as new therapeutic tool, CD44 targeted based, of glioblastoma multiforme", J. Cell Physiol., 2018; 233: 6550-6564) (Year: 2018).*
Chen et al. "Progress and Chellenges in Transfer of Large-Area Graphene Films" Adv. Sci. 2016 3:1500343 pp. 1-15.
Lee et al., "Enhancement of biostability and mechanical properties of hyaluronic acid hydrogels by tannic acid treatment" Carbohydrate Polymers 2018 186:290-298.

* cited by examiner

*Primary Examiner* — Leigh C Maier
*Assistant Examiner* — Everett White
(74) *Attorney, Agent, or Firm* — LICATA & TYRRELL P.C.

(57) ABSTRACT

The present invention relates to a water degradable film comprising hyaluronic acid or a salt thereof and polyphenol compounds. The film of the present invention can transcribe nanofilms in the form of CNT (carbon nanotube), graphene and magnetic particles to various places. The film of the present invention can be dissolved by an aqueous solution or body fluid, and can be effectively used in the medical field since it is non-toxic and biocompatible. The film of the present invention can also be effectively used as a transcript that does not degrade the quality and performance of the device because no residue remains in the electronic device and the existing photolithography process.

7 Claims, 26 Drawing Sheets

WATER DEGRADABLE FILM CONTAINING HYALURONIC ACID OR SALT THEREOF AND POLYPHENOL COMPOUNDS

CROSS-REFERENCES TO RELATED APPLICATION

This patent application claims the benefit of priority under 35 U.S.C. § 119 from Korean Patent Application No. 10-2019-0111716 filed on Sep. 9, 2019, the contents of which are incorporated herein by reference.

BACKGROUND OF THE INVENTION

1. Field of the Invention

The present invention relates to a water degradable film, particularly to a water degradable film comprising hyaluronic acid or a salt thereof and polyphenol compounds.

2. Description of the Related Art

The interest in biodegradable polymers is increasing day by day due to the desire for life extension, increased interest in the environment, pollution problems of synthetic plastics, and increased demand for artificial organs and medical materials. Accordingly, studies on biocompatible and biodegradable polymers are being actively conducted, and these biodegradable polymers are divided into natural polymers and synthetic polymers.

The biodegradable natural polymers include chitosan, hyaluronic acid, flurane, and dextran. Since these are natural polymers, they have few side effects in the human body and each has its own advantages, but their physical properties are very weak, and it is difficult to achieve a desired purpose by carrying a therapeutic drug alone.

Particularly, hyaluronic acid (HA) is a colorless, high viscosity polysaccharide in which glucuronic acid, a repeating unit, and N-acetylglucosamine are alternately combined, and is naturally produced in organisms. Hyaluronic acid is a part of the extracellular matrix and is used in various medical applications due to its properties as a lubricant in joints, eyes, etc. Specifically, hyaluronic acid derivatives have been developed for various purposes, such as post-surgical adhesion barriers, anti-wrinkle agents, cosmetic aids, joint function improvers, drug carriers and cell culture supports (Scaffold), and in particular, active research is being conducted on anti-wrinkle agents and cosmetic aids for commercial use. In addition, hyaluronic acid exhibits excellent biocompatibility and moisturizing effect and excellent lubrication effect on physical friction, so it is often used as a cosmetic additive.

However, since hyaluronic acid dissolves very quickly in aqueous environments or body fluids, its modification is essential for various applications. There are many types of modification methods. For example, there is a method for producing a soluble form of hyaluronic acid derivatized with tyramine, which forms an insoluble hydrogel network upon addition of a cross-linking agent. In addition, the solubility of the hyaluronic acid chain can be lowered by binding a hydrophobic group thereto. Then, these derivatives become insoluble in the aqueous medium (depending on the molecular weight and the degree of substitution of the hydrophobic chain), and are generally soluble in mixtures of water and organic solvents.

As one of the hyaluronic acid derivatives, the hyaluronic acid cross-linked product in which hyaluronic acids are cross-linked using a cross-linking agent has excellent biocompatibility, physical stability, and biodegradability. The hyaluronic acid cross-linked product can be prepared in various forms such as microbeads, seals, hydrogels, films, and sponges. But, the hyaluronic acid cross-linked product has a relatively low stability against hyaluronic acid degrading enzymes and heat, and it is difficult to remove non-reactive chemicals, so there is a limit to its use as a high purity biocompatible material.

In addition, the representative synthetic polymers with biodegradability include the U.S. FDA-approved poly(lactide) (PLA) and poly(glycolide) (PGA), and their copolymer poly(lactide-co-glycolide) (PLGA). Compared to the natural polymers, the synthetic polymers have improved properties and are easy to carry therapeutic drugs, but lack the ability to selectively act on target cells or tissues, so they have problems of affecting normal cells or normal tissues.

On the other hand, in order to freely handle nanomaterials, especially nanofilms (for example, 100 nm thick SWCNT film with magnetic nanoparticles), there is a need for a technique to remove the nanofilm using a tape and then move it to a desired location. For example, it is expected that various applications will be possible if the nanofilm can be detached using a 3M tape and attached it to the brain of a mouse. However, the 3M tape is a synthetic polymer that does not benefit and does not melt in the body.

Patent Reference 1 describes a self-supporting, biodegradable film based on hydrophobized hyaluronic acid, a method of preparation and a use thereof. However, the film described in Patent Reference 1 cannot be decomposed in and out of the body by moisture, and thus there is a problem that is difficult to remove in vivo.

PRIOR ART REFERENCE

Patent Reference (Patent Reference 1) Korean Patent Publication No. 10-2017-0128351

SUMMARY OF THE INVENTION

It is an object of the present invention to provide a water degradable film.

It is another object of the present invention to provide a water degradable film capable of transferring or transcribing nanomaterials.

It is another object of the present invention to provide a preparation method of a water degradable film capable of transferring or transcribing nanomaterials.

It is another object of the present invention to provide a method for transferring or transcribing nanomaterials.

To achieve the above objects, in an aspect of the present invention, the present invention provides a water degradable film comprising hyaluronic acid or a salt thereof and polyphenol compounds, wherein the polyphenol compounds are interposed between at least a part of the polymer main chains through hydrogen bonding.

In another aspect of the present invention, the present invention provides a water degradable film for transferring or transcribing nanomaterials comprising a nanomaterial; and a water degradable film comprising hyaluronic acid or a salt thereof and polyphenol compounds, wherein the polyphenol compounds are interposed between at least a part of the polymer main chains through hydrogen bonding.

In another aspect of the present invention, the present invention provides a preparation method of a water degradable film for transferring or transcribing nanomaterials comprising the following steps:

preparing an aqueous solution by mixing hyaluronic acid or its salt and polyphenol compounds in water (step 1);

applying the aqueous solution of step 1 on the substrate introduced with nanomaterials (step 2);

forming a film by drying the substrate of step 2 (step 3); and separating the film prepared in step 3 from the substrate (step 4).

In another aspect of the present invention, the present invention provides a method for transferring or transcribing nanomaterials comprising the following steps:

attaching the water degradable film for transferring or transcribing nanomaterials to a location where nanomaterials are to be introduced; and decomposing and removing the film using water.

Advantageous Effect

The water degradable film comprising hyaluronic acid or a salt thereof and polyphenol compounds of the present invention can transcribe nanofilms in the form of CNT (carbon nanotube), graphene and magnetic particles to various places. The film of the present invention can be dissolved by an aqueous solution or body fluid, and can be effectively used in the medical field since it is non-toxic and biocompatible. The film of the present invention can also be effectively used as a transcript that does not degrade the quality and performance of the device because no residue remains in the electronic device and the existing photolithography process.

BRIEF DESCRIPTION OF THE DRAWINGS

FIG. 9b is a photograph showing the water degradable film for transferring or transcribing nanomaterials prepared by applying the water degradable film comprising a hyaluronic acid polymer and tannic acid on the structure prepared in FIG. 9a.

DESCRIPTION OF THE PREFERRED EMBODIMENTS

Figure 1:
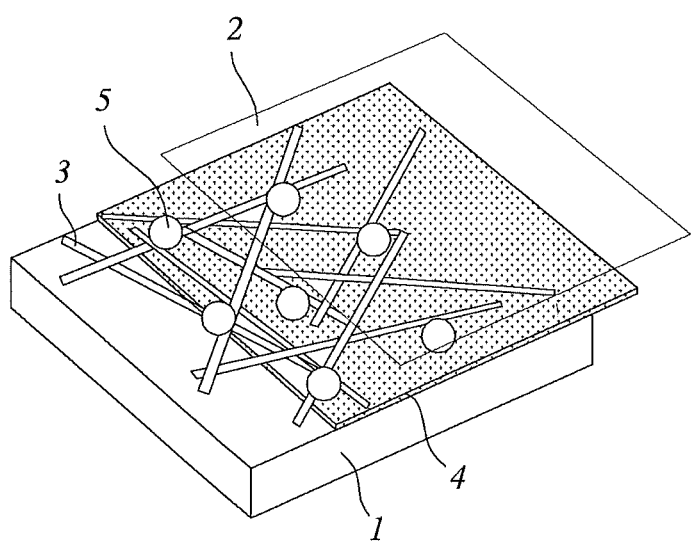
FIG. 1 is a schematic diagram showing the water degradable film for transferring or transcribing nanomaterials comprising a nanomaterial and a water degradable film, prepared on a silicon substrate.

Hereinafter, the present invention is described in detail.

In an aspect of the present invention, the present invention provides a water degradable film comprising hyaluronic acid or a salt thereof and polyphenol compounds, wherein the polyphenol compounds are interposed between at least a part of the polymer main chains through hydrogen bonding.

The film can include the polyphenol compound in an amount of 0.05 to 10 weight part, preferably 0.1 to 5 weight part, and more preferably 0.3 to 1 weight part based on 1 weight part of hyaluronic acid or its salt.

The polyphenol compound can be one or more compounds selected from the group consisting of tannic acid, isoflavone, catechin, curcumin, tannin, hydroxy benzoic acid, hydroxy cinnamic acid, flavonoid, lignan, stilbene, caffeic acid, chlorogenic acid, anthocyan, pyrogallol, ellagic acid, gallic acid, theaflavin-3-gallate, resveratrol, kaempferol, quercetin, myricetin, luteolin, delphinidin, cyanidin, ampelopsin, hesperidin, aurantinidine, europinidin, pelargonidin, malvidin, peonidin, petunidin and rosinidin.

The film can be biodegradable.

Particularly, the film of the present invention uses hyaluronic acid and a polyphenol compound having high water solubility, so it can be decomposed by an aqueous solution or moisture, body fluids, and the like.

When the film of the present invention is applied to the medical field, it is easy to remove the film after transcribing (or transferring) the desired nanomaterial in vivo or ex vivo. Therefore, it can be used as an alternative for the conventional nanofilm. In addition, the film of the present invention can be used as a transcript for the transcription of nanomaterials in the electronics industry, such as device processing as well as the medical field.

The film can be prepared according to the preparation method of a water degradable film comprising the following steps:

preparing an aqueous solution by mixing hyaluronic acid or its salt and polyphenol compounds in water (step 1);

applying the aqueous solution of step 1 on a substrate (step 2);

forming a film by drying the substrate of step 2 (step 3); and separating the film prepared in step 3 from the substrate (step 4).

Hereinafter, the preparation method is described in detail.

Step 1 is a step of preparing an aqueous solution by adding and dissolving hyaluronic acid or its salt and polyphenol compounds in water. At this time, the dissolution of step 1 can be performed by sonication, but not always limited thereto.

In step 1, a hyaluronic acid polymer having a molecular weight of 1.3 to 1.8 Mda can be used, and tannic acid, isoflavone, catechin or curcumin can be used as a polyphenol compound, but not always limited thereto.

In addition, the polyphenol compound can be used in an amount of 0.05 to 10 weight part, preferably 0.1 to 5 weight part, and more preferably 0.3 to 1 weight part based on 1 weight part of hyaluronic acid or its salt.

Step 2 is a step of applying the aqueous solution on a substrate. The application can be performed by a coating method. The coating method can be one method selected from the group consisting of spin coating, dip coating, roll coating, screen coating, spray coating, spin casting, flow coating, screen printing, inkjet and drop casting. In an embodiment of the present invention, a solution was applied on a substrate according to a spin coating method, and then rotated at high speed to dry to prepare a water degradable film, but not always limited thereto.

Step 3 is a step of preparing a film by drying the solution coated on the substrate. The drying can be performed using $N_2$ gas or on a hot plate in the range of 50 to 90° C., and the drying time is not particularly limited, but is preferably 20 to 60 minutes.

Step 4 is a step of separating the dried film to finally obtain a film.

In another aspect of the present invention, the present invention provides a water degradable film for transferring or transcribing nanomaterials comprising a nanomaterial; and a water degradable film comprising hyaluronic acid or a salt thereof and polyphenol compounds, wherein the polyphenol compounds are interposed between at least a part of the polymer main chains through hydrogen bonding.

The nanomaterial can be one or more selected from the group consisting of nanowire, nanorod, nanosheet, nanoplate, nanosphere, nanotube, nanodiamond, nanofiber, nanoneedle, nanoparticle, and nanofilm.

The nanoparticle can be nanoparticle of any metal selected from the group consisting of platinum, aluminum, tin, lead, silver, copper, iron, cobalt, nickel, molybdenum, tungsten, selenium, tellurium, oxides thereof, and combinations and alloys thereof; semiconductor nanoparticle, magnetic nanoparticle, etc., but not always limited thereto.

In an embodiment of the present invention, CNT nanofilm, graphene nanosheet, graphene oxide nanofilm, CNT nanofilm in which magnetic nanoparticles are introduced, and the like were used, but not always limited thereto.

In addition, a detailed description of the water degradable film of the water degradable film for transferring or transcribing nanomaterials is the same as the specific description of the water degradable film.

In an embodiment of the present invention, it was confirmed that the water degradable film for transferring or transcribing nanomaterials transferred the CNT nanofilm to PDMS without leaving residues. This indicates that the water degradable film for transferring or transcribing nanomaterials of the present invention can be effectively used in the medical field or the electronics industry (see Example 1 and Experimental Example 1-1).

In an embodiment of the present invention, it was confirmed that the water degradable film for transferring or transcribing nanomaterials transferred the CNT nanofilm to cardiac muscle cells of a neonatal rat without residues. It was also confirmed that the transferred CNT nanofilm stimulated heart cells by applying electricity since it had electrical conductivity. These indicate that the water degradable film for transferring or transcribing nanomaterials of the present invention can be effectively used in the medical field (see Example 1 and Experimental Example 1-2).

In an embodiment of the present invention, it was confirmed that the water degradable film for transferring or transcribing nanomaterials transferred the graphene oxide nanofilm to the silicon substrate without residues. It was also confirmed that several nanometer nanomaterials could be handled through the water degradable film for transferring or transcribing nanomaterials. These indicate that the water degradable film for transferring or transcribing nanomaterials of the present invention can be effectively used as a transcript in the electronics industry (see Example 1 and Experimental Example 2).

In an embodiment of the present invention, it was confirmed that the water degradable film was not removed by acetone or an organic solvent when the water degradable film for transferring or transcribing nanomaterials was attached on the photoresist line pattern and the photoresist was removed with acetone in the photolithographic process. This means that the water degradable film attached line pattern was formed. When another material to form a pattern on the water degradable film attached line pattern was coated and washed with water, the water degradable film was decomposed, and as a result, another material pattern could be formed. That is, since the water degradable film for transferring or transcribing nanomaterials of the present invention can be applied to a photolithographic process to form patterns of various materials, it can be effectively used in the electronics industry (see Example 1 and Experimental Example 3).

In addition, the film of the present invention uses hyaluronic acid and a polyphenol compound having high water solubility, so it can be decomposed by an aqueous solution or moisture, body fluids, and the like.

When the film of the present invention is applied to the medical field, it is easy to remove the film after transcribing (or transferring) the desired nanomaterial in vivo or ex vivo. In addition, the film of the present invention is biocompatible and has an effect that does not cause side effects, so it can be effectively used in the medical field. FIGS. 10a-10e show the application examples for this.

The water degradable film for transferring or transcribing nanomaterials of the present invention comprises hyaluronic acid or a salt thereof and a polyphenol compound, wherein the polyphenol compound is interposed between at least a part of the polymer main chains through hydrogen bonding. Since the nanomaterial is attached to the water degradable film, the film can be attached to the desired position to introduce the nanomaterial, and then the water degradable film is removed with water to introduce the nanomaterial to the desired position. Therefore, the film of the present invention can be effectively used in the electronics industry, such as the manufacture of electronic devices. FIGS. 9a~9c and 11a~11c show the application examples for this.

Conventionally, it is well known to transcribe graphene using PMMA (Poly(methyl methacrylate)). But in this case, PMMA is not sufficiently washed out with acetone, which degrades the quality of graphene and degrades device performance.

On the other hand, the water degradable film for transferring or transcribing nanomaterials of the present invention can be removed with an aqueous solution or water after attaching the nanomaterial to a desired position, so that the nanomaterial can be transcribed or transferred without residues.

Therefore, the film of the present invention can be effectively used in the electronics industry. In particular, when transferring the CNT and graphene films in electronic device processes and photolithography processes, the water degradable film for transferring or transcribing nanomaterials of the present invention can replace the photoresist and PMMA polymers.

In another aspect of the present invention, the present invention provides a preparation method of a water degradable film for transferring or transcribing nanomaterials comprising the following steps:

preparing an aqueous solution by mixing hyaluronic acid or its salt and polyphenol compounds in water (step 1);

applying the aqueous solution of step 1 on the substrate introduced with nanomaterials (step 2);

forming a film by drying the substrate of step 2 (step 3); and separating the film prepared in step 3 from the substrate (step 4).

Hereinafter, the preparation method of the film is described in detail.

Step 1 is a step of preparing an aqueous solution by adding and dissolving hyaluronic acid or its salt and polyphenol compounds in water. At this time, the dissolution of step 1 can be performed by sonication, but not always limited thereto.

In step 1, a hyaluronic acid polymer having a molecular weight of 1.3 to 1.8 Mda can be used, and tannic acid, isoflavone, catechin or curcumin can be used as a polyphenol compound, but not always limited thereto.

In addition, the polyphenol compound can be used in an amount of 0.05 to 10 weight part, preferably 0.1 to 5 weight part, and more preferably 0.3 to 1 weight part based on 1 weight part of hyaluronic acid or its salt.

Step 2 is a step of applying the aqueous solution on a substrate. The application can be performed by a coating method. The coating method can be one method selected from the group consisting of spin coating, dip coating, roll coating, screen coating, spray coating, spin casting, flow coating, screen printing, inkjet and drop casting. In an embodiment of the present invention, a solution was applied on a substrate according to a spin coating method, and then rotated at high speed to dry to prepare a water degradable film, but not always limited thereto.

In addition, a detailed description of the nonmaterial is the same as the specific description of the nonmaterial in the water degradable film for transferring or transcribing nanomaterials.

Step 3 is a step of preparing a film by drying the solution coated on the substrate. The drying can be performed using $N_2$ gas or on a hot plate in the range of 50 to 90° C., and the drying time is not particularly limited, but is preferably 20 to 60 minutes.

Step 4 is a step of separating the dried film to finally obtain a film.

In another aspect of the present invention, the present invention provides a method for transferring or transcribing nanomaterials comprising the following steps:

attaching the water degradable film for transferring or transcribing nanomaterials to a location where nanomaterials are to be introduced; and decomposing and removing the film using water.

Hereinafter, the present invention will be described in detail by the following preparative examples, examples and experimental examples.

However, the following preparative examples, examples and experimental examples are only for illustrating the present invention, and the contents of the present invention are not limited thereto.

Preparative Example 1: Preparation of CNT (Carbon Nanotube) Nanofilm

A CNT nanofilm that can be transcribed or transferred by the water degradable film for transferring or transcribing nanomaterials was prepared as follows.

Step 1: Purification Process and Acid Treatment of CNT (Carbon Nanotube)

After adding 40 mg of a single wall carbon nanotube (ASP-100F, Hanwha Chemical Co.) to a solution containing 10 ml of nitric acid and 30 ml of sulfuric acid, ultrasonic treatment was performed for 4 hours to remove the metal catalyst present in the carbon nanotube. After filtering the acid treated carbon nanotube solution with an anodic aluminum oxide membrane filter having a diameter of 200 nm, the filtered carbon nanotube was washed with tertiary distilled water to neutralize to pH 7. The washed carbon nanotube was dispersed in 250 ml of an aqueous solution in which Triton X-100, a surfactant, was dispersed at the concentration of 3 wt %, and then sonicated for 1 hour. Thereafter, to remove impurities such as a transition metal catalyst and amorphous carbon, centrifugation was performed at 6000 rpm for 1 hour. The supernatant was taken to obtain an aqueous solution containing a carbon nanotube modified with a carboxyl group and a surfactant. The aqueous solution was filtered with an anodic aluminum oxide membrane filter and the surfactant was removed using 1 L of methanol, which was then dispersed in chloroform.

Figure 5A:
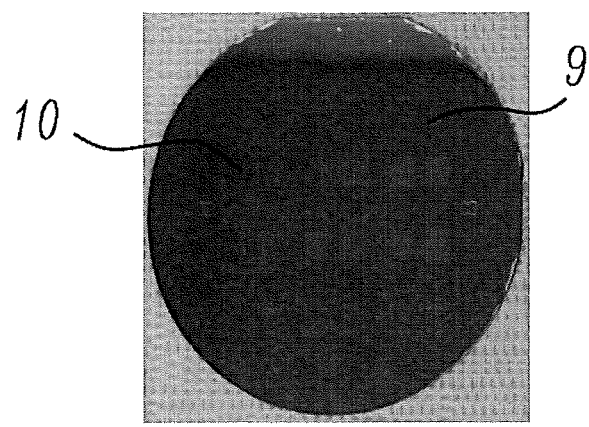
FIG. 5a is a photograph showing the CNT nanofilm introduced on a silicon substrate.
Figure 5B:
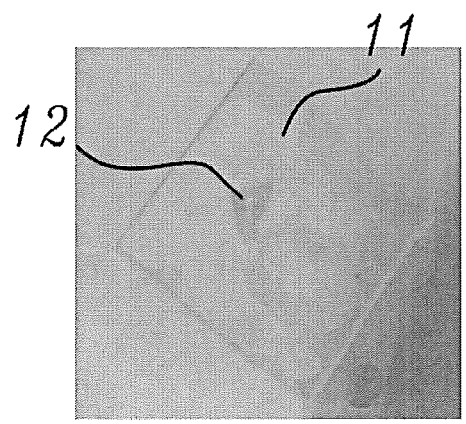
FIG. 5b is a photograph showing the water degradable film for transferring or transcribing nanomaterials attached to PDMS (polydimethylsiloxane) being decomposed by water, and the CNT nanofilm remaining on the PDMS.
Figure 6A:
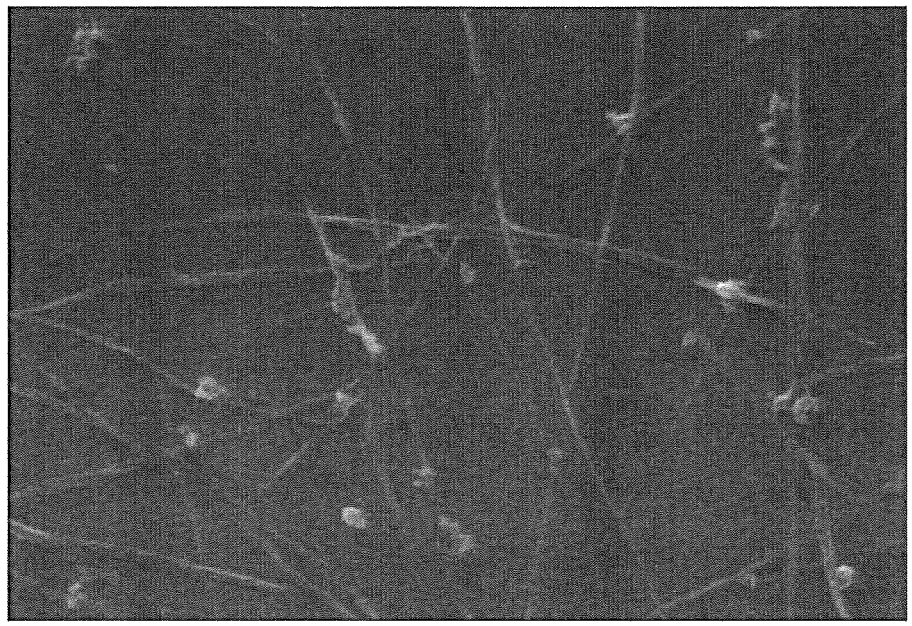
FIG. 6a is a scanning electron microscope photograph showing the conventional bare CNT nanofilm.
Figure 6B:
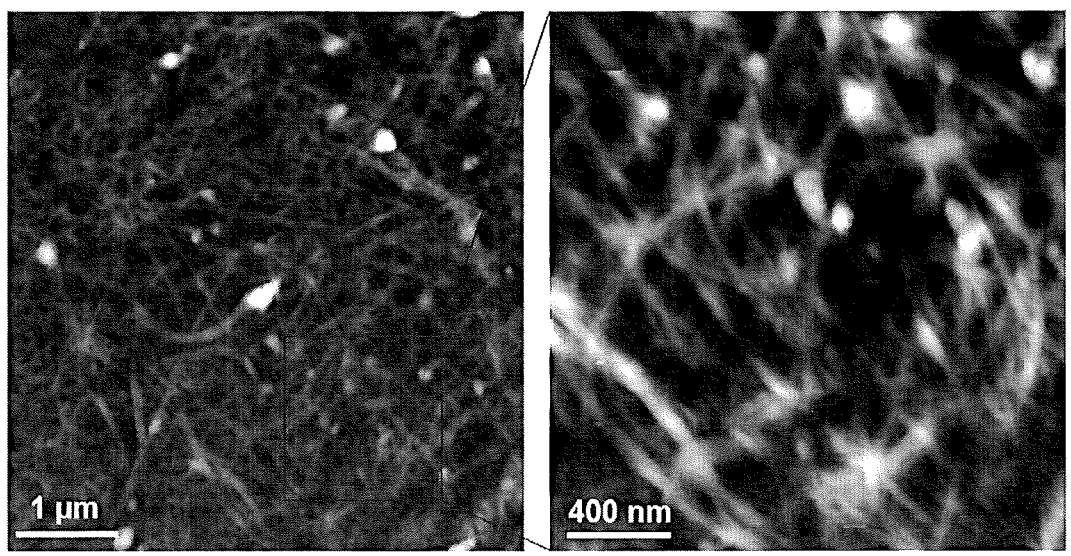
FIG. 6b is a set of images showing the CNT nanofilm transferred to PDMS, obtained by AFM (atomic force microscopy).

Step 2: Preparation of CNT Nanofilm by Filtration 4 ml of the carbon nanotube solution dispersed in chloroform prepared in step 1 (concentration: 0.1 mg/ml) was filtered with an anodic aluminum oxide membrane filter having a diameter of 200 nm to remove chloroform, and the carbon nanotube was laminated in the form of a network structure on the upper layer of the filter. The laminated carbon nanotube was dried in an oven at 105° C. for 3 hours to vaporize the residual chloroform. A silicon wafer substrate was placed on the bottom of the 3M sodium hydroxide aqueous solution, and the carbon nanotube laminated anodic aluminum oxide membrane filter was placed on the substrate for 4 hours. The anodic aluminum oxide membrane was dissolved and removed by the sodium hydroxide aqueous solution. Tertiary distilled water was slowly added to the sodium hydroxide aqueous solution to neutralize the pH to 7, and the residual aqueous solution was removed using an aspirator while maintaining the pH at 7. As a result, a CNT (carbon nanotube) nanofilm introduced on a silicon wafer substrate was obtained (see FIG. 5a).

Preparative Example 2: Preparation of Graphene Oxide Nanofilm

A grapheme oxide nanofilm that can be transcribed or transferred by the water degradable film for transferring or transcribing nanomaterials was prepared according to Langmuir-Blogett technique as follows.

A graphene oxide solution was prepared by adding 0.1 g of graphene oxide to 100 ml of tertiary distilled water and dissolving thereof by ultrasonic treatment.

Figure 8A:
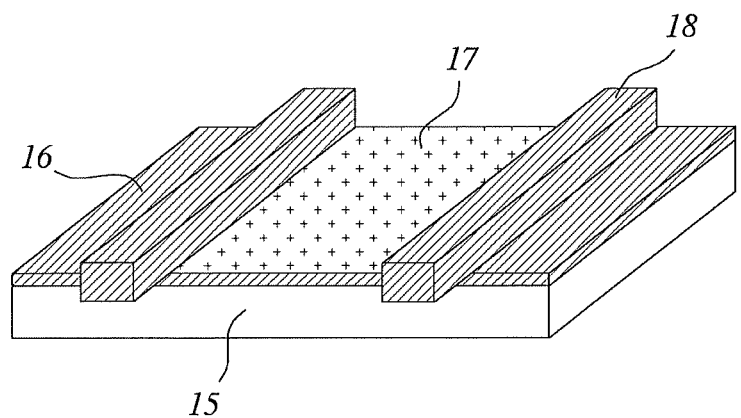
FIG. 8a is a schematic diagram showing the preparation of a graphene oxide nanofilm on a silicon substrate using a Langmuir-Blogett technique.
Figure 8B:
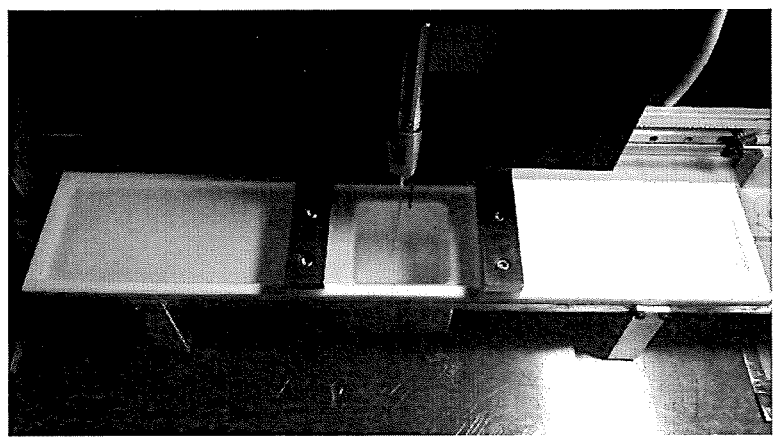
FIG. 8b is a photograph showing the preparation of a graphene oxide nanofilm on a silicon substrate using a Langmuir-Blogett technique.
Figure 8C:
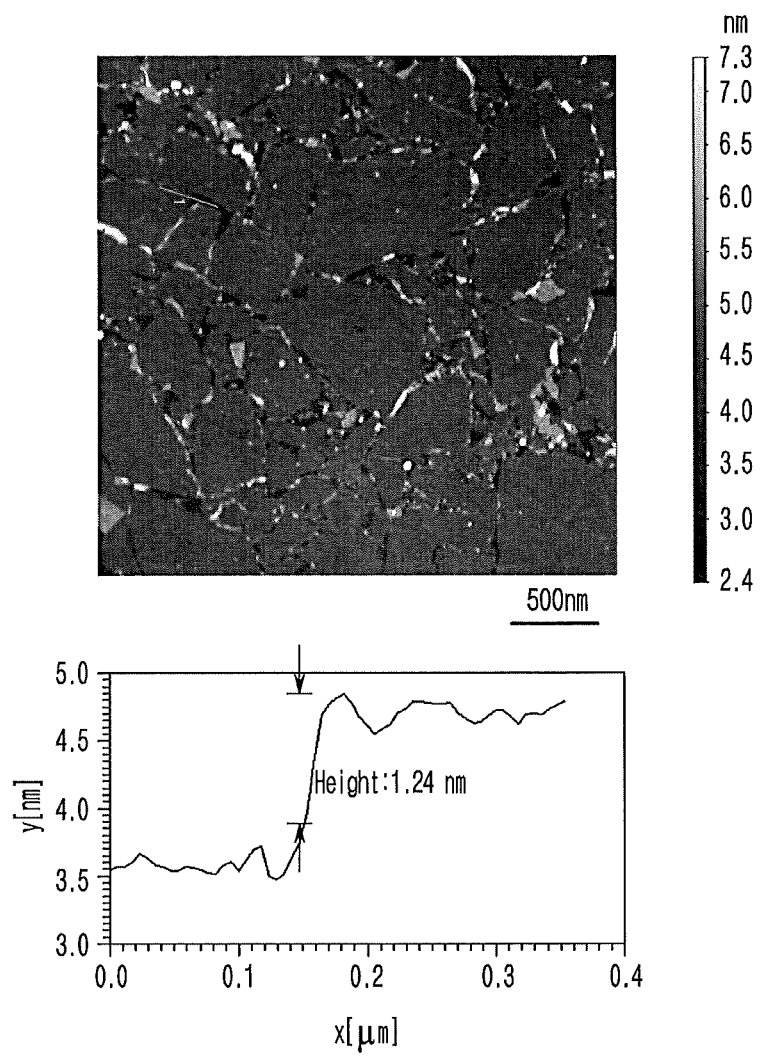
FIG. 8c is a set of an image showing the graphene oxide nanofilm observed with AFM (atomic force microscopy), and a graph showing the observation results thereof.

After mixing the solution (concentration: 1 mg/ml) with 4 ml of methanol, 200 µl of the mixed solution was applied dropwise to the Langmuir-Blodgett trough containing tertiary distilled water using a micro syringe dropwise, and the mixture was placed at room temperature for 30 minutes to vaporize methanol. Then, barriers on both sides of the Langmuir-Blodgett trough were collected at the speed of 4 mm/min. As a result, a graphene oxide nanofilm was prepared as a thin film of uniform shape under the surface pressure of 13 mN/m (see FIGS. 8a~8c).

Example 1: Preparation of Water Degradable Film Comprising Tannic Acid

<1-1> Preparation of Water Degradable Film Comprising Hyaluronic Acid Polymer and Tannic Acid To prepare a water degradable film, an aqueous solution in which a hyaluronic acid polymer and tannic acid were mixed was prepared. Particularly, 0.6 g of a hyaluronic acid polymer (molecular weight: 1.3~1.8 Mda) and 0.6 g of tannic acid (molecular weight: 1701.19 g/mol) were added to 30 ml of tertiary distilled water and dissolved by ultrasonic treatment. As a result, an aqueous solution in which 4 wt % of a hyaluronic acid polymer and tannic acid were mixed was prepared. The chemical structures of the hyaluronic acid polymer and tannic acid used in the aqueous solution are shown below.

Figure 2A:
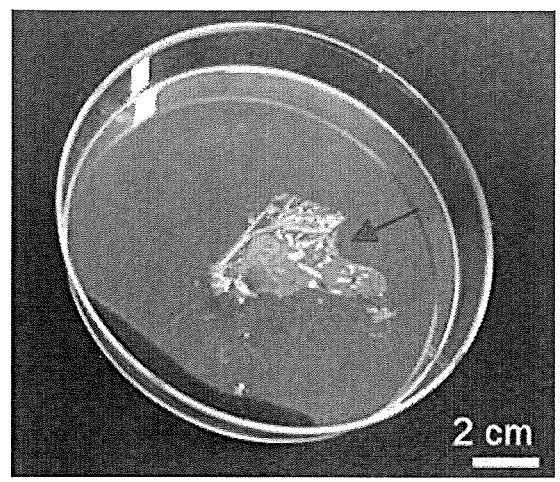
FIG. 2a is a photograph showing the water degradable film comprising a hyaluronic acid polymer and tannic acid.
Figure 3:
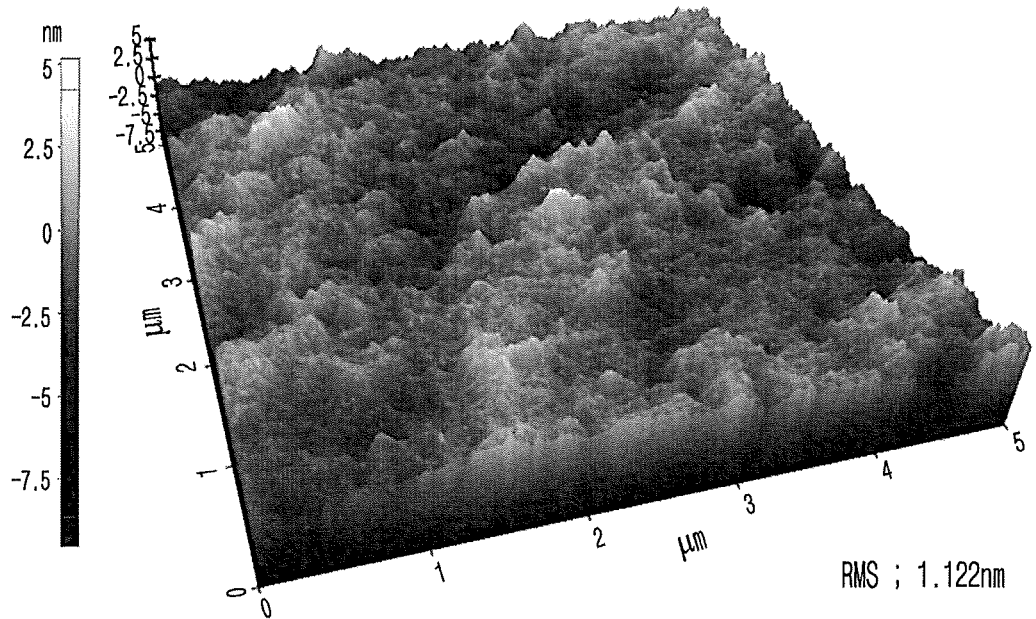
FIG. 3 is an image showing the water degradable film comprising a hyaluronic acid polymer and tannic acid, obtained by AFM (atomic force microscopy).

A water degradable film containing a hyaluronic acid polymer and tannic acid can be obtained by spin-coating the aqueous solution. When the water degradable film was observed with an atomic force microscope (AFM) capable of viewing the nanostructure, the surface roughness (Rq) value was 0.367 nm, indicating that the water degradable film is very flat (see FIGS. 2a and 3).

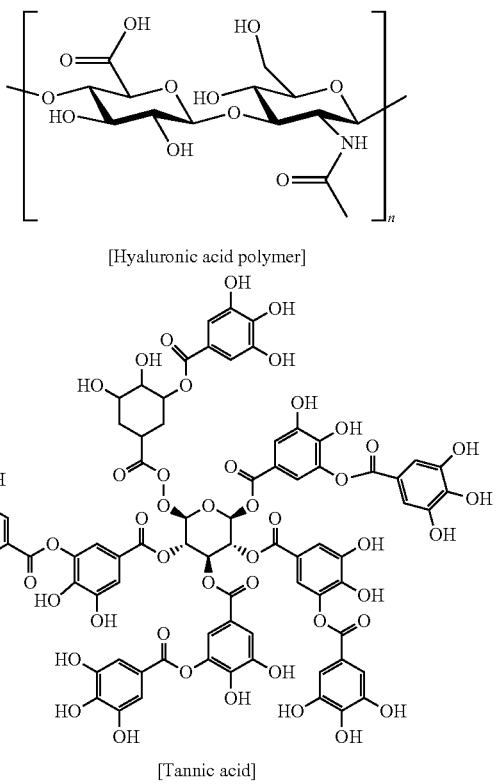

[Hyaluronic acid polymer]

[Tannic acid]

Figure 4:
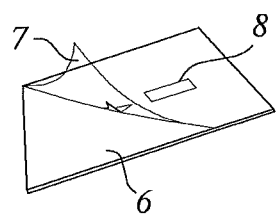
FIG. 4 is a schematic diagram showing that the water degradable film is applied on a CNT nanofilm introduced on a silicon wafer substrate.

<1-2> Preparation of Water Degradable Film for Transferring or Transcribing Nanomaterials Comprising Tannic Acid The CNT (carbon nanotube) nanofilm prepared in Preparative Example 1 or the graphene oxide nanofilm prepared in Preparative Example 2 was placed in a spin coater. 100 µl of the aqueous solution was dropped thereto, which was rotated at 3000 rpm for 30 seconds, followed by heat treatment at 50° C. for 30 minutes using a heating stirrer. As a result, a water degradable film for transferring or transcribing nanomaterials comprising a CNT (carbon nanotube) nanofilm or a graphene oxide nanofilm as a nanomaterial; and a water degradable film containing a hyaluronic acid polymer and tannic acid was prepared (see FIG. 4).

Example 2: Preparation of Water Degradable Film Comprising Isoflavone

To prepare a water degradable film, an aqueous solution in which a hyaluronic acid polymer and isoflavone were mixed was prepared. Particularly, 0.3 g of a hyaluronic acid polymer (molecular weight: 1.3~1.8 Mda) and 0.1 g of isoflavone (molecular weight: 222.24 g/mol) were added to 30 ml of tertiary distilled water and dissolved by ultrasonic treatment. As a result, an aqueous solution in which 1.33 wt % of a hyaluronic acid polymer and isoflavone were mixed was prepared. The chemical structures of the hyaluronic acid polymer and isoflavone used in the aqueous solution are shown below.

Figure 2B:
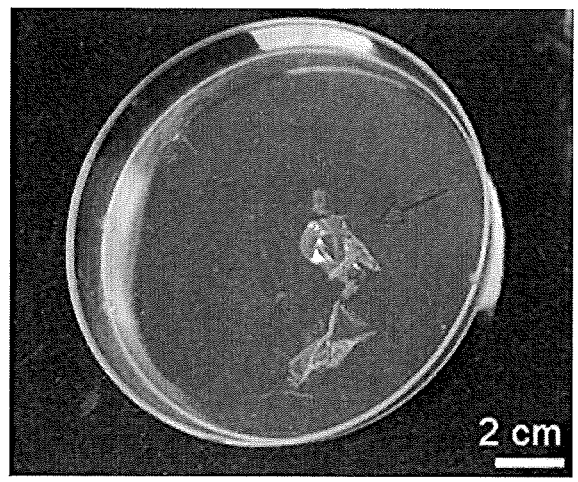
FIG. 2b is a photograph showing the water degradable film comprising a hyaluronic acid polymer and isoflavone.

A PS (polystyrene) substrate was placed in a spin coater. 100 µl of the aqueous solution was dropped thereto, which was rotated at 3000 rpm for 30 seconds, followed by heat treatment at 50° C. for 30 minutes using a heating stirrer. As a result, a water degradable film comprising a hyaluronic acid polymer and isoflavone was prepared (see FIG. 2b).

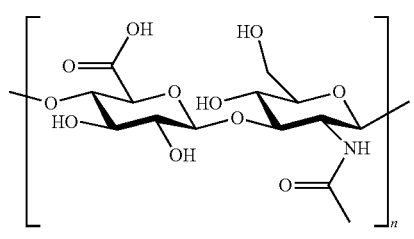

[Hyaluronic acid polymer]

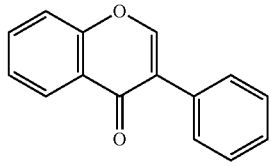

[isoflavone]

Example 3: Preparation of Water Degradable Film Comprising Catechin

To prepare a water degradable film, an aqueous solution in which a hyaluronic acid polymer and catechin were mixed was prepared. Particularly, 0.3 g of a hyaluronic acid polymer (molecular weight: 1.3~1.8 Mda) and 0.1 g of catechin (molecular weight: 290.26 g/mol) were added to 30 ml of tertiary distilled water and dissolved by ultrasonic treatment. As a result, an aqueous solution in which 1.33 wt % of a hyaluronic acid polymer and catechin were mixed was prepared. The chemical structures of the hyaluronic acid polymer and catechin used in the aqueous solution are shown below.

Figure 2C:
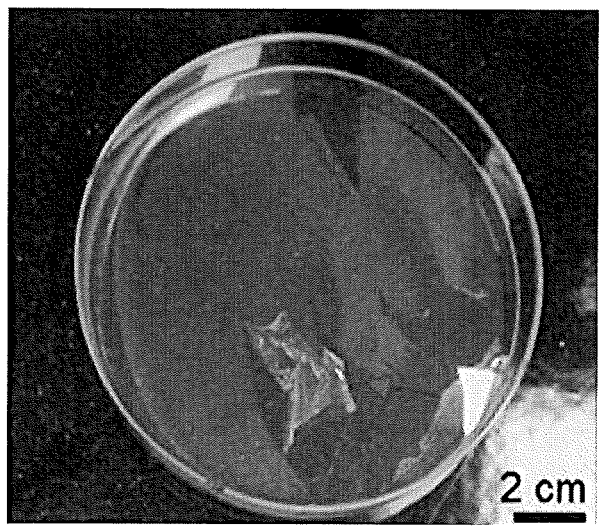
FIG. 2c is a photograph showing the water degradable film comprising a hyaluronic acid polymer and catechin.

A PS (polystyrene) substrate was placed in a spin coater. 100 μl of the aqueous solution was dropped thereto, which was rotated at 3000 rpm for 30 seconds, followed by heat treatment at 50° C. for 30 minutes using a heating stirrer. As a result, a water degradable film comprising a hyaluronic acid polymer and catechin was prepared (see FIG. 2c).

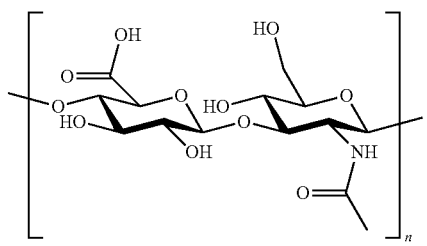

[Hyaluronic acid polymer]

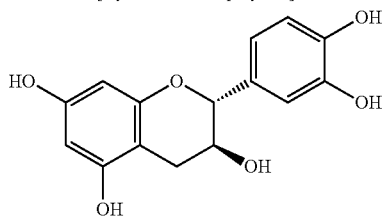

[catechin]

Example 4: Preparation of Water Degradable Film Comprising Curcumin

To prepare a water degradable film, an aqueous solution in which a hyaluronic acid polymer and curcumin were mixed was prepared. Particularly, 0.3 g of a hyaluronic acid polymer (molecular weight: 1.3~1.8 Mda) and 0.1 g of curcumin (molecular weight: 368.38 g/mol) were added to 30 ml of tertiary distilled water and dissolved by ultrasonic treatment. As a result, an aqueous solution in which 1.33 wt % of a hyaluronic acid polymer and curcumin were mixed was prepared. The chemical structures of the hyaluronic acid polymer and curcumin used in the aqueous solution are shown below.

Figure 2D:
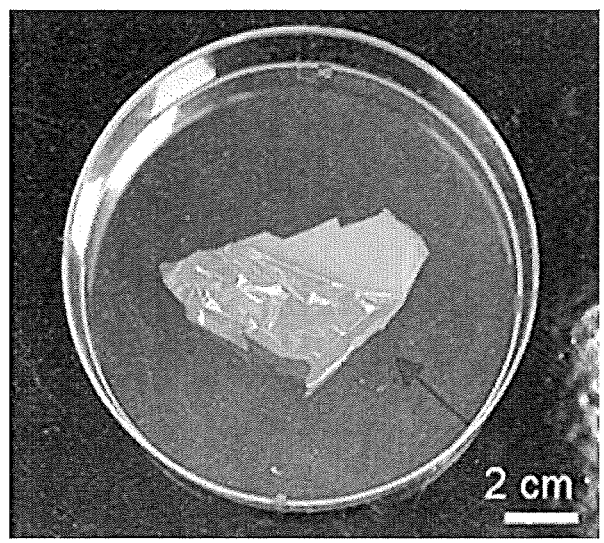
FIG. 2d is a photograph showing the water degradable film comprising a hyaluronic acid polymer and curcumin.

A PS (polystyrene) substrate was placed in a spin coater. 100 μl of the aqueous solution was dropped thereto, which was rotated at 3000 rpm for 30 seconds, followed by heat treatment at 50° C. for 30 minutes using a heating stirrer. As a result, a water degradable film comprising a hyaluronic acid polymer and curcumin was prepared (see FIG. 2d).

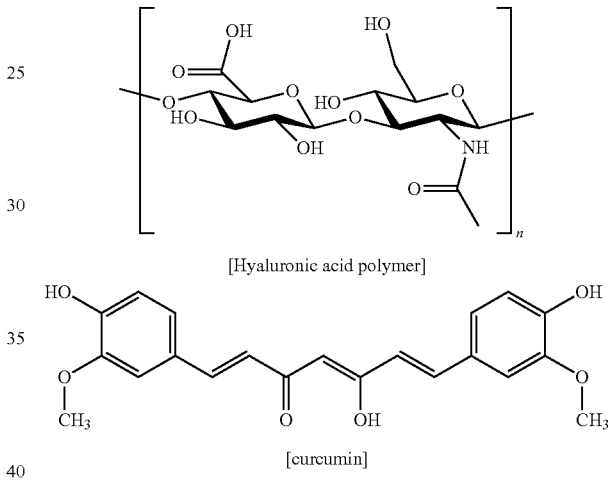

[Hyaluronic acid polymer]

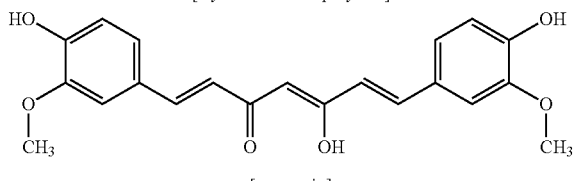

[curcumin]

Experimental Example 1: Transcription of CNT Nanofilm Using Water Degradable Film for Transferring or Transcribing Nanomaterials In order to confirm that the water degradable film for transferring or transcribing nanomaterials according to the present invention has the effect of transferring or transcribing nanomaterials, an experiment of transcribing the CNT nanofilm to PDMS (polydimethylsiloxane) or cardiac muscle cells of a neonatal rat was performed as follows. The results are shown in FIGS. 5a, 5b, 6a, 6b, and 10a~10e.

<1-1> Transcription of CNT Nanofilm to PDMS (Polydimethylsiloxane)

Figure 7:
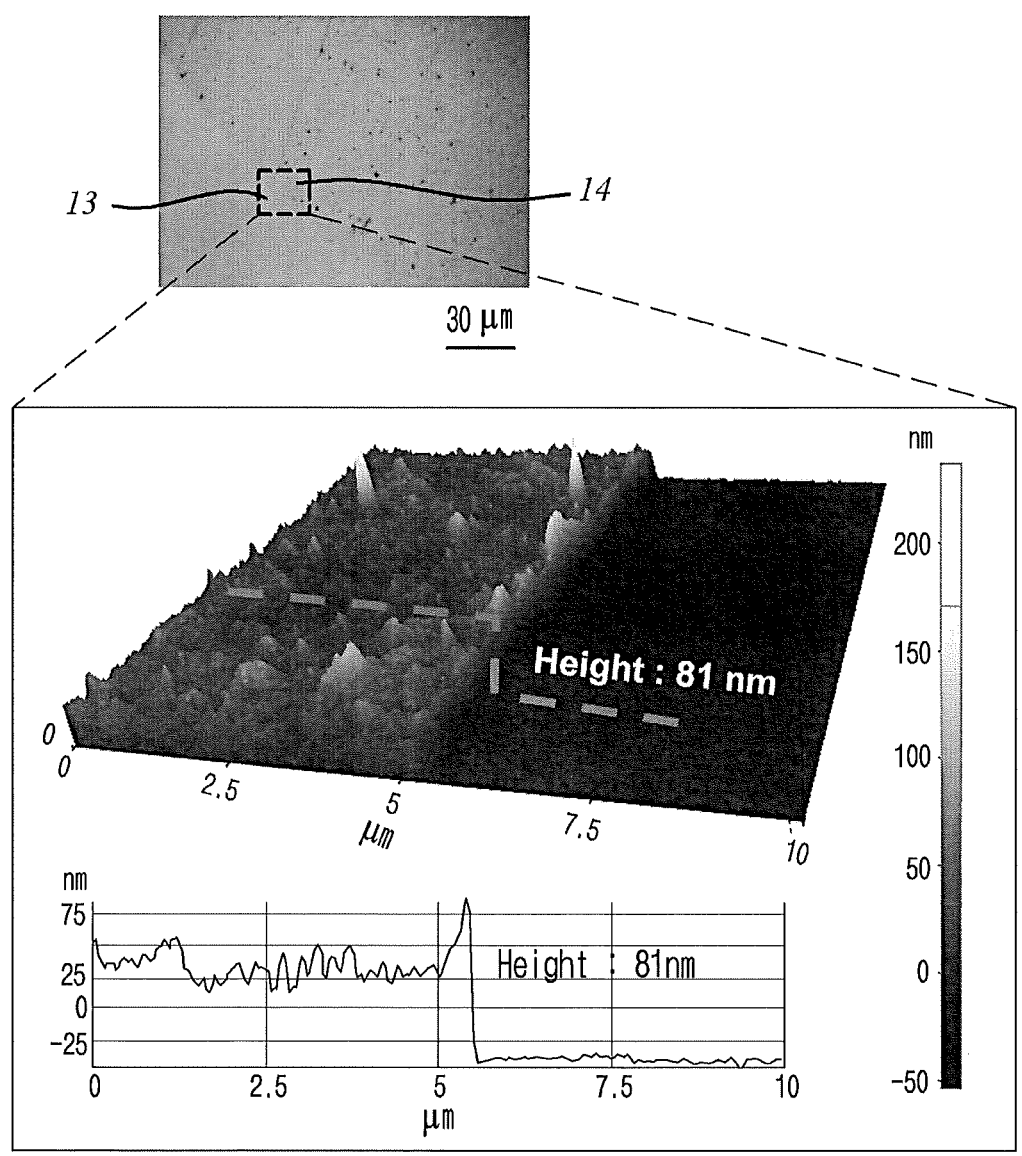
FIG. 7 is a set of an image showing the edge of the CNT nanofilm transferred to PDMS observed with AFM, and a graph showing the observation results thereof.

The water degradable film for transferring or transcribing nanomaterials comprising the CNT nanofilm prepared in Preparative Example 1; and a water degradable film containing a hyaluronic acid polymer and tannic acid was attached to PDMS (polydimethylsiloxane) and immersed in distilled water for 3 to 5 minutes. As a result, the water degradable film containing a hyaluronic acid polymer and tannic acid was decomposed by water, and the CNT nanofilm transferred to PDMS remained (see FIG. 5b). The images of the CNT nanofilm transferred to the PDMS observed with AFM (atomic force microscopy) were compared with the photographs of scanning electron microscope of the conventional bare CNT. As a result, it was confirmed that the water degradable film containing a hyaluronic acid polymer and tannic acid was decomposed (see FIGS. 6a and 6b). In addition, the edge portion of the CNT nanofilm transferred to PDMS was observed with AFM. As a result, the thickness of the CNT nanofilm was about 81 nm, and the edge portion was neatly formed, confirming that the water degradable film was decomposed (see FIG. 7).

The results indicate that the water degradable film containing hyaluronic acid or its salt and polyphenol compound was dissolved and disappeared by water in or out of the body, so that no residue remained and the nanomaterial could be transferred to the desired place and remained. Therefore, it was confirmed that the water degradable film for transferring or transcribing nanomaterials of the present invention can be effectively used in the medical field or the electronics industry.

<1-2> Transcription of CNT Nanofilm to Neonatal Rat Cardiac Muscle Cells

Cardiac muscle cells of a neonatal rat were grown in a general cell culture container (TCPS, tissue culture polystyrene). The water degradable film for transferring or transcribing nanomaterials comprising the CNT nanofilm prepared in Preparative Example 1; and a water degradable film containing a hyaluronic acid polymer and tannic acid was attached to the cardiac muscle cells, and immersed in distilled water. As a result, the water degradable film containing a hyaluronic acid polymer and tannic acid was decomposed by water, and the CNT nanofilm transferred to the cardiac muscle cells (see FIG. 10a).

The CNT nanofilm transferred to the cardiac muscle cells was observed with AFM. As a result, it was confirmed that the cell flection of the cardiac muscle cells was about 427 nm deep, and that the water degradable film was decomposed without residues (see FIGS. 10d and 10e). In addition, the transferred CNT nanofilm was analyzed by FT-Raman spectroscopy (Fourier Transform Raman Spectroscopy). As a result, D band, G band, and G' band, the Raman peaks, were 1350 $cm^{-1}$, 1573 $cm^{-1}$, and 2687 $cm^{-1}$, respectively, which are the characteristic Raman peaks of the CNT nanofilm. Therefore, it was confirmed that the CNT nanofilm was transferred to the cardiac muscle cells (see FIG. 10b). It was also confirmed that electricity flows through the CNT nanofilm transferred to the neonatal rat cardiac muscle cells (see FIG. 10c).

The above results indicate that the water degradable film for transferring or transcribing nanomaterials can transfer the nanomaterial to a highly curved portion such as a cell or a biological tissue without leaving residues. In addition, it shows that the CNT nanofilm has electrical conductivity and can stimulate cardiac cells by applying electricity. Therefore, it was confirmed that the water degradable film for transferring or transcribing nanomaterials of the present invention can be effectively used in the medical field.

Figure 9A:
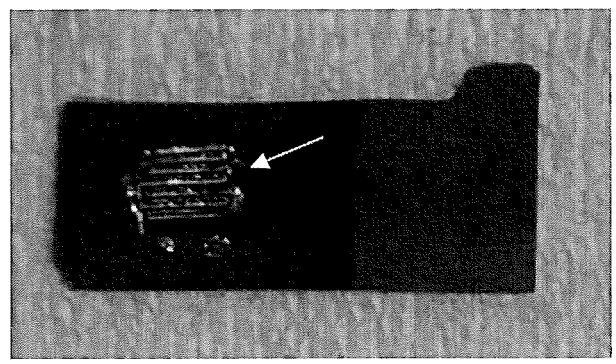
FIG. 9a is a photograph showing the structure in which gold electrodes are deposited on the graphene oxide nanofilm.
Figure 9B:
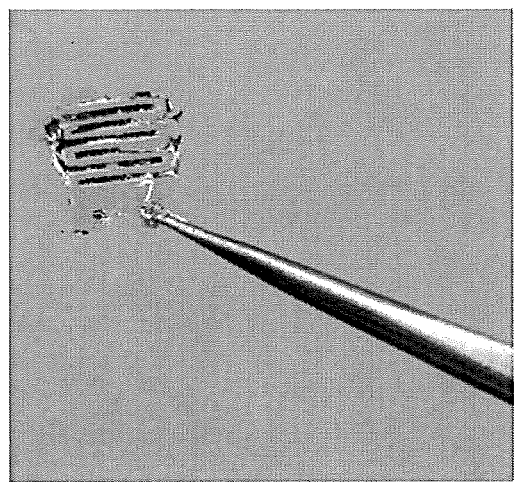
Figure 9C:
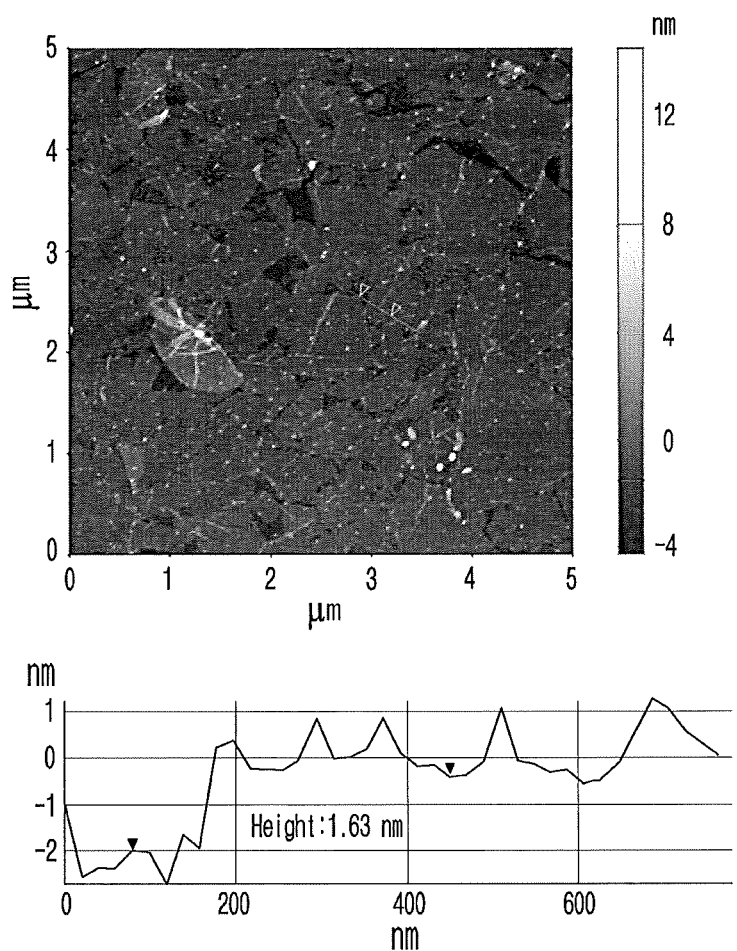
FIG. 9c is a set of an image showing the graphene oxide film transferred to a silicon substrate after the water degradable film comprising a hyaluronic acid polymer and tannic acid was removed observed with AFM, and a graph showing the observation results thereof.
Figure 10A:
FIG. 10a is a photograph showing the film for transferring or transcribing nanomaterials applied on cardiac muscle cells of a neonatal rat observed with an optical microscope.
Figure 10B:
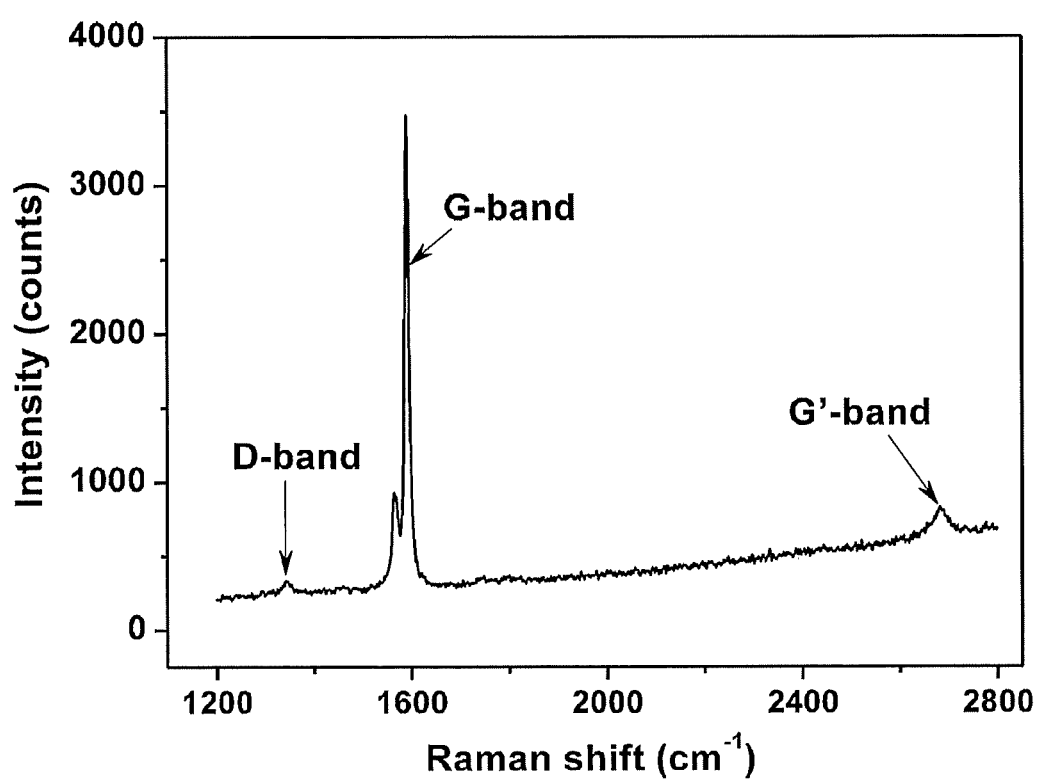
FIG. 10b is a graph showing the results of analyzing the transferred CNT nanofilm by FT-Raman spectroscopy (Fourier Transform Raman Spectroscopy).
Figure 10C:
FIG. 10c is a photograph showing that the CNT nanofilm transferred to cardiac muscle cells of a neonatal rat, after the water degradable film was decomposed by water, is electrified.
Figure 10D:
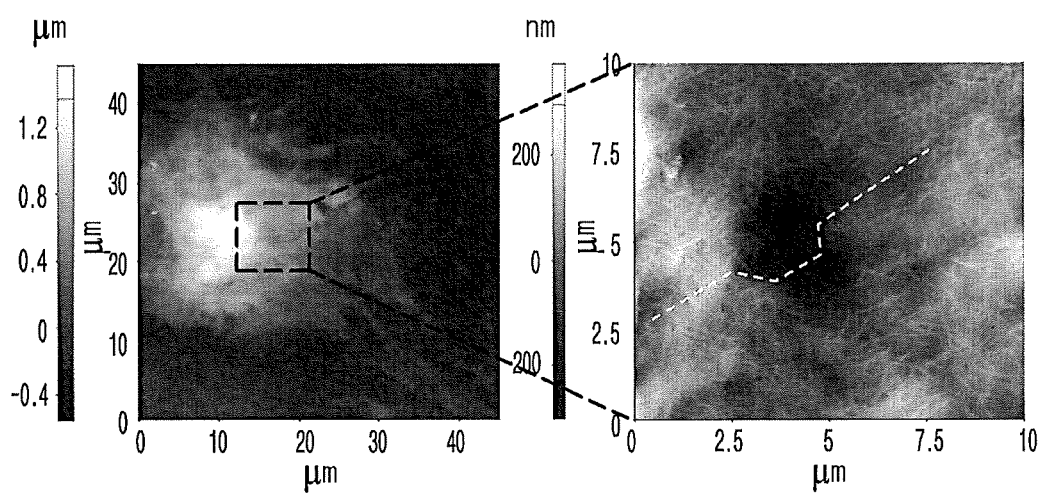
FIG. 10d is a set of images showing the CNT nanofilm transferred to cardiac muscle cells of a neonatal rat observed with AFM.
Figure 10E:
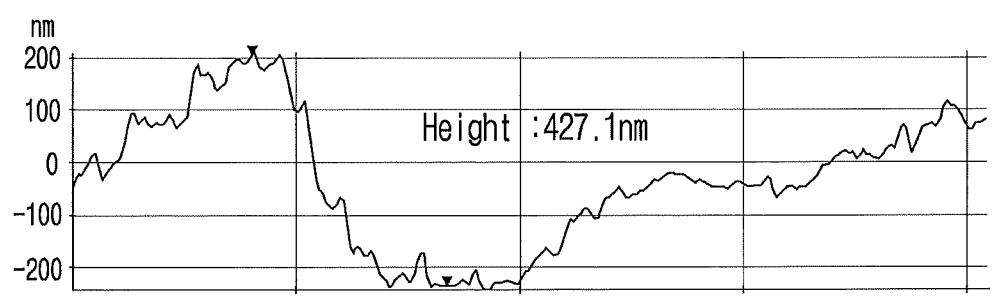
FIG. 10e is a graph showing the results of observation of the CNT nanofilm transferred to cardiac muscle cells of a neonatal rat using AFM.

Experimental Example 2: Transcription of Grapheme Oxide Nanofilm Using Water Degradable Film for Transferring or Transcribing Nanomaterials In order to confirm that the water degradable film for transferring or transcribing nanomaterials according to the present invention has the effect of transferring or transcribing nanomaterials, an experiment of transferring the graphene oxide nanofilm to a silicon substrate was performed as follows. The results are shown in FIGS. 9a~9c.

Gold electrodes were deposited on the graphene oxide nanofilm prepared in Preparative Example 2. A water degradable film for transferring or transcribing nanomaterials was prepared according to the method of Example 1, except that the above structure was used (see FIGS. 9a and 9b). The film was attached to the silicon substrate, and immersed in distilled water. As a result, the water degradable film containing a hyaluronic acid polymer and tannic acid was decomposed by water, and the graphene oxide nanofilm transferred to the silicon substrate. The graphene oxide nanofilm transferred to the silicon substrate was observed with AFM. As a result, it was confirmed that the thickness of the graphene oxide nanofilm was about 2 nm, and the water degradable film was decomposed without residues (see FIG. 9c).

The above results indicate that the water degradable film containing hyaluronic acid or its and polyphenol compounds had excellent ability to separate nanomaterials. After the water degradable film transferred or transcribed the nanomaterial to the desired position, it was dissolved and disappeared by water in or out of the body, so that no residue remained and the nanomaterial could be transferred to the desired place. Therefore, it was confirmed that the water degradable film for transferring or transcribing nanomaterials of the present invention can be effectively used in various industrial fields, especially in the medical field or the electronics industry field.

Figure 11A:
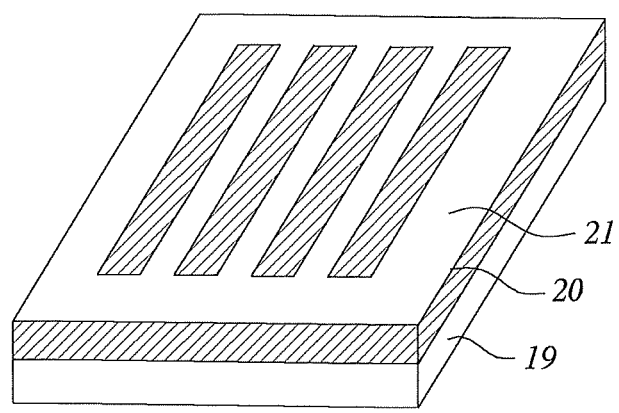
FIG. 11a is a schematic diagram showing the photoresist (PR) line pattern formed on a silicon substrate.
Figure 11B:
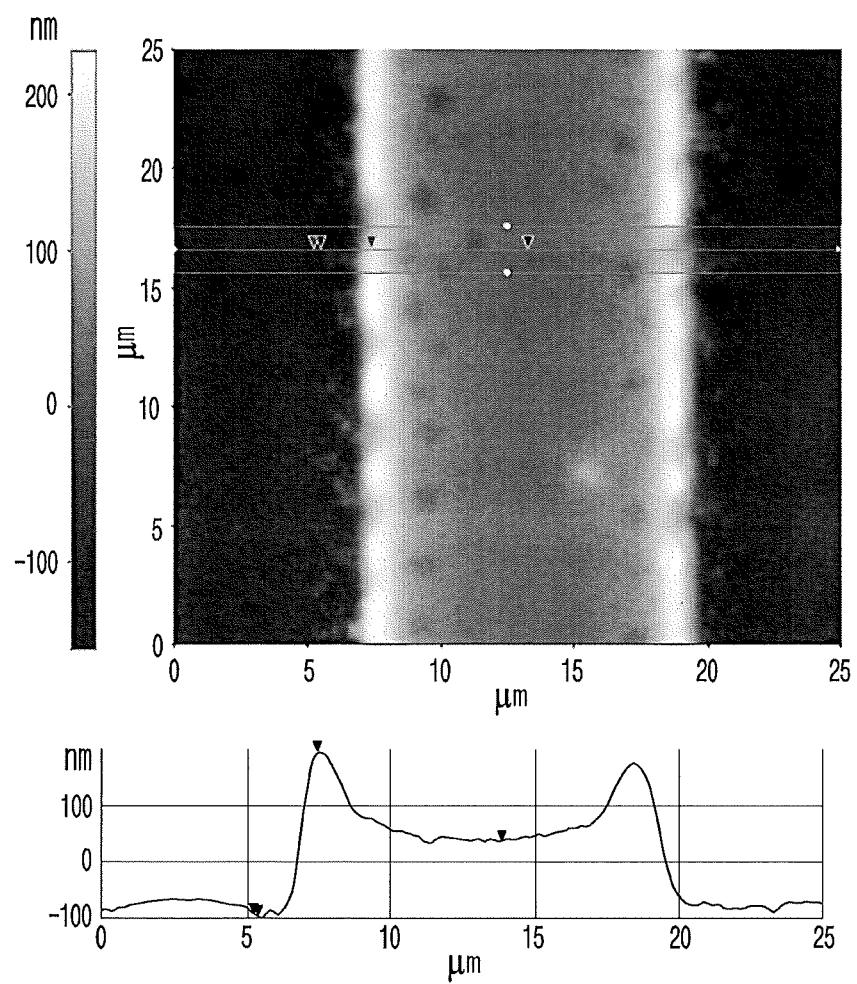
FIG. 11b is an image showing the water degradable film remaining after removing the photoresist with acetone and applying the water degradable film for transferring or transcribing nanomaterials on the photoresist line pattern, observed with AFM.
Figure 11C:
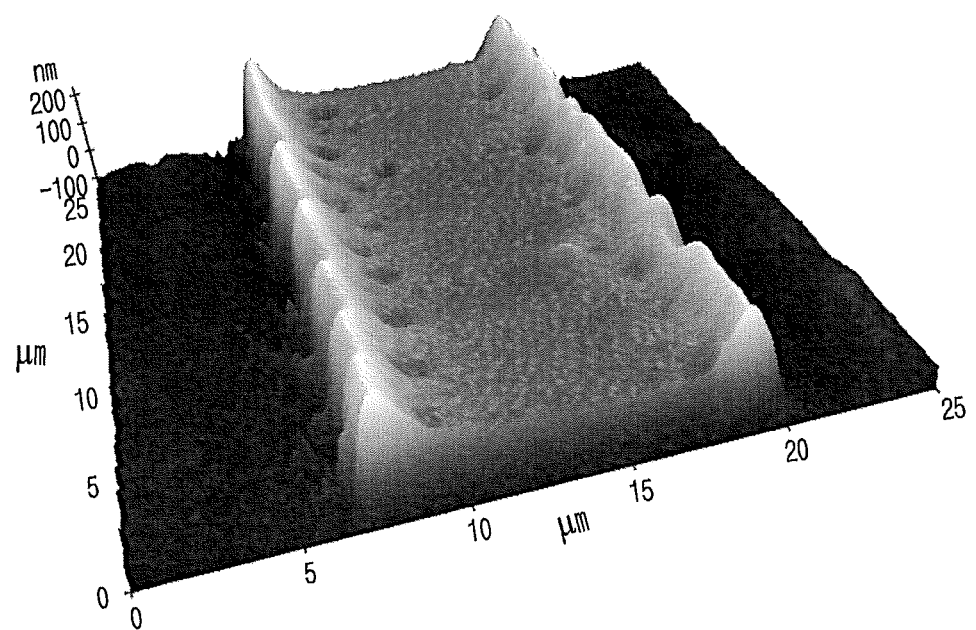
FIG. 11c is a set of an image showing the remaining water degradable film observed with AFM, and a graph showing the observation results thereof.

Experimental Example 3: Use of Water Degradable Film for Transferring or Transcribing Nanomaterials in Photolithography Process In order to confirm whether the water degradable film for transferring or transcribing nanomaterials according to the present invention can be used in the photolithographic process, an experiment was performed as follows. The results are shown in FIGS. 11a~11c.

The water degradable film was attached on the photoresist (PR) line pattern formed on the silicon substrate, and the photoresist was removed with acetone. As a result, it was confirmed that the water degradable film was not removed by acetone or an organic solvent. The water degradable film was observed with AFM. As a result, it was confirmed that the water degradable film having a diameter of 25 μm and a thickness of 100 nm remained not decomposed by acetone (see FIGS. 11a~11c).

This means that the water degradable film attached line pattern was formed.

When another material to form a pattern on the water degradable film attached line pattern was coated and washed with water, the water degradable film was decomposed, and as a result, another material pattern could be formed.

That is, since the water degradable film for transferring or transcribing nanomaterials of the present invention can be applied to a photolithographic process to form patterns of various materials, it can be effectively used in the electronics industry.

In the case of the conventional photoresist process, the photoresist is removed using a toxic organic solvent, which is expensive in treating wastewater and causes environmental pollution. In the photolithography process, if the water degradable film for transferring or transcribing nanomaterials of the present invention is used instead of the conventional photoresist process, it is decomposed by an aqueous solution, so that a toxic organic solvent may not be used, and it does not cause the above problems because it is environmentally friendly. Therefore, the water degradable film for transferring or transcribing nanomaterials of the present invention can be effectively used in the electronics industry field such as the photolithography process.

BRIEF DESCRIPTION OF THE MARK OF DRAWINGS

1: silicon substrate
2: water degradable film
3: CNT nanofilm
4: graphene or graphene oxide film
5: magnetic nanoparticle
6: silicon substrate
7: water degradable film
8: CNT nanofilm
9: silicon substrate
10: CNT nanofilm
11: PDMS (polydimethylsiloxane)
12: CNT nanofilm
13: PDMS
14: CNT nanofilm
15: Langmuir-Blodgett trough
16: water face
17: graphene oxide film
18: barrier
19: Si (back gate)
20: SiO$_2$
21: photoresist (PR)

What is claimed is:

1. A water degradable film for transferring or transcribing nanomaterials without leaving residues, said water degradable film consisting of:
    a nanomaterial; and
    a water degradable film consisting of hyaluronic acid or a salt thereof and a polyphenol compound, wherein the polyphenol compound is bonded to at least a part of the hyaluronic acid main chains through hydrogen bonding,
    wherein the nanomaterial comprises one or more selected from the group consisting of carbon nanotube, graphene, graphene oxide and magnetic nanoparticle, and
    wherein the polyphenol compound is one or more compounds selected from the group consisting of tannic acid, isoflavone, catechin, curcumin, tannin, hydroxy benzoic acid, hydroxy cinnamic acid, flavonoid, lignan, stilbene, caffeic acid, chlorogenic acid, anthocyan, pyrogallol, ellagic acid, gallic acid, theaflavin-3-gallate, resveratrol, kaempferol, quercetin, myricetin, luteolin, delphinidin, cyanidin, ampelopsin, hesperidin, aurantinidine, europinidin, pelargonidin, malvidin, peonidin, petunidin and rosinidin.

2. The water degradable film for transferring or transcribing nanomaterials without leaving residues according to claim 1, wherein the nanomaterial is any one form selected from the group consisting of nanowire, nanorod, nanosheet, nanoplate, nanosphere, nanotube, nanodiamond, nanofiber, nanoneedle, nanoparticle and nanofilm.

3. A preparation method of a water degradable film of claim 1 comprising the following steps:
    (a) preparing an aqueous solution by mixing hyaluronic acid or its salt and the polyphenol compound in water;
    (b) applying the aqueous solution of step 1 on the substrate introduced with the nanomaterials;
    (c) forming the water degradable film of claim 1 on the substrate by drying the substrate of step (b); and
    (d) separating the film prepared in step (c) from the substrate.

4. The preparation method according to claim 3, wherein the polyphenol compound is mixed in an amount of 0.05 to 10 weight part based on 1 weight part of the hyaluronic acid or its salt in step (a).

5. A method for transferring or transcribing nanomaterials without leaving residues comprising the following steps:
    attaching the water degradable film of claim 1 to a selected location where nanomaterials are to be introduced; and
    decomposing and removing the film using water so that only the nanomaterial remains at the selected location.

6. The water degradable film according to claim 1, wherein the film includes the polyphenol compound in an amount of 0.05 to 10 weight part based on 1 weight part of the hyaluronic acid or its salt.

7. The water degradable film according to claim 1, wherein the film is characterized in that it is biodegradable.

* * * * *